(12) United States Patent  
Richardson et al.

(10) Patent No.: US 8,523,940 B2
(45) Date of Patent: Sep. 3, 2013

(54) ANNULOPLASTY RING WITH ANCHORS FIXED BY CURING POLYMER

(75) Inventors: Leonard B. Richardson, Brooklyn Park, MN (US); Kevin D. Edmunds, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 98 days.

(21) Appl. No.: 13/242,953

(22) Filed: Sep. 23, 2011

(65) Prior Publication Data

US 2012/0296419 A1 Nov. 22, 2012

Related U.S. Application Data

(60) Provisional application No. 61/487,083, filed on May 17, 2011.

(51) Int. Cl.
*A61F 2/24* (2006.01)
(52) U.S. Cl.
USPC ........................................ 623/2.37; 623/2.36
(58) Field of Classification Search
USPC ....................................... 623/2.36, 2.37, 2.38
See application file for complete search history.

(56) References Cited

U.S. PATENT DOCUMENTS

| | | | |
|---|---|---|---|
| 5,064,431 A | 11/1991 | Gilbertson et al. | |
| 5,441,516 A | 8/1995 | Wang et al. | |
| 5,449,372 A | 9/1995 | Schmaltz et al. | |
| 5,836,968 A | 11/1998 | Simon et al. | |
| 5,855,565 A | 1/1999 | Bar-Cohen et al. | |
| 5,980,570 A * | 11/1999 | Simpson | 623/2.11 |
| 6,270,515 B1 | 8/2001 | Linden et al. | |
| 6,391,054 B2 | 5/2002 | Carpentier et al. | |
| 6,432,131 B1 | 8/2002 | Ravenscroft | |
| 6,517,584 B1 | 2/2003 | Lecalve | |
| 6,619,291 B2 | 9/2003 | Hlavka et al. | |
| 6,676,702 B2 | 1/2004 | Mathis | |
| 6,682,546 B2 | 1/2004 | Amplatz | |
| 6,689,164 B1 | 2/2004 | Seguin | |
| 6,726,716 B2 | 4/2004 | Marquez | |
| 6,743,219 B1 | 6/2004 | Dwyer et al. | |

(Continued)

FOREIGN PATENT DOCUMENTS

DE 102007043831 A1 4/2009
WO 03/075748 9/2003

(Continued)

OTHER PUBLICATIONS

Search Report and Written Opinion for PCT Application No. PCT/US2011/52976, mailed Jun. 1, 2012.

(Continued)

*Primary Examiner* — David Isabella
*Assistant Examiner* — Dinah Baria
(74) *Attorney, Agent, or Firm* — Vidas, Arrett & Steinkraus, P.A.

(57) ABSTRACT

Annuloplasty rings and methods for inserting annuloplasty rings are herein disclosed. The annuloplasty ring has a ring shell and a plurality of anchoring fasteners for anchoring the ring shell to adjacent heart tissue. To maintain the shape of the annuloplasty ring upon attachment of the ring to the patient's heart, a hardening polymer is inserted into the ring shell, which is permitted to cure, thereby providing support for the annuloplasty ring and the patient's heart valve.

5 Claims, 11 Drawing Sheets

(56) References Cited

U.S. PATENT DOCUMENTS

| | | |
|---|---|---|
| 6,921,407 B2 | 7/2005 | Nguyen et al. |
| 6,997,951 B2 | 2/2006 | Solem et al. |
| 7,060,021 B1 | 6/2006 | Wilk |
| 7,118,595 B2 | 10/2006 | Ryan et al. |
| 7,201,761 B2 | 4/2007 | Woolfson et al. |
| 7,296,577 B2 | 11/2007 | Lashinske et al. |
| 7,431,726 B2 | 10/2008 | Spence et al. |
| 7,635,386 B1 | 12/2009 | Gammie |
| 7,637,944 B2 | 12/2009 | Ryan et al. |
| 7,655,015 B2 | 2/2010 | Goldfarb et al. |
| 7,717,954 B2 | 5/2010 | Solem et al. |
| 2003/0078465 A1 | 4/2003 | Pai et al. |
| 2004/0148021 A1 | 7/2004 | Cartledge et al. |
| 2004/0215230 A1 | 10/2004 | Frazier et al. |
| 2004/0236419 A1 | 11/2004 | Milo |
| 2004/0243230 A1 | 12/2004 | Navia et al. |
| 2005/0065550 A1 | 3/2005 | Starksen et al. |
| 2005/0065601 A1 | 3/2005 | Lee et al. |
| 2005/0107812 A1 | 5/2005 | Starksen et al. |
| 2005/0137696 A1 | 6/2005 | Salahieh et al. |
| 2005/0222488 A1 | 10/2005 | Chang et al. |
| 2006/0276891 A1 | 12/2006 | Nieminen et al. |
| 2007/0027533 A1* | 2/2007 | Douk .......................... 623/2.11 |
| 2007/0027536 A1 | 2/2007 | Mihaljevic et al. |
| 2007/0066993 A1 | 3/2007 | Kreidler |
| 2007/0080188 A1 | 4/2007 | Spence et al. |
| 2007/0112422 A1 | 5/2007 | Dehdashtian |
| 2007/0244556 A1 | 10/2007 | Rafiee et al. |
| 2007/0244557 A1 | 10/2007 | Rafiee et al. |
| 2008/0045977 A1 | 2/2008 | To et al. |
| 2008/0051840 A1 | 2/2008 | Moaddeb et al. |
| 2008/0065203 A1 | 3/2008 | Khalapyan |
| 2009/0177277 A1 | 7/2009 | Milo |
| 2010/0030014 A1 | 2/2010 | Ferrazzi |
| 2010/0121435 A1 | 5/2010 | Subramanian et al. |
| 2010/0280604 A1 | 11/2010 | Zipory et al. |
| 2010/0324669 A1 | 12/2010 | Hlavka et al. |
| 2012/0123531 A1* | 5/2012 | Tsukashima et al. ........ 623/2.37 |

FOREIGN PATENT DOCUMENTS

| | | |
|---|---|---|
| WO | 2005055883 A1 | 6/2005 |
| WO | 2009/135022 | 11/2009 |
| WO | 2010091383 A2 | 8/2010 |
| WO | 2010091653 A1 | 8/2010 |

OTHER PUBLICATIONS

Search Report and Written Opinion for PCT Application No. PCT/US2012/030711, mailed Jun. 13, 2012.

Search Report and Written Opinion for PCT Application No. PCT/US2011/52865, mailed Jun. 13, 2012.

AMPLATZER Multifenestrated Septal Occluder—"Cribriform", 2007-2010 AGA Medical Corporation, Plymouth, MN.

Amplatzer Septal Occluder and Delivery System, 2007-2010 AGA Medical Corporation, Plymouth, MN.

Simon Nitinol Filter Versatile and Dependable Performance, simon__vena__cava__filter.htm, Copyright 2004 C. R. Bard, Inc.

amplatzer__web__page__20101005.aspx.htm, viewed on Oct. 5, 2010.

U.S. Appl. No. 61/487,065, entitled "Percutaneous Mitral Annulus Mini-Plication," and filed on May 17, 2011.

U.S. Appl. No. 61/487,053, entitled "Positioning Cage," and filed on May 17, 2011.

U.S. Appl. No. 61/487,063, entitled "Corkscrew Annuloplasty Device," and filed on May 17, 2011.

U.S. Appl. No. 61/487,072 "Annuloplasty Ring with Piercing Wire and Segmented Wire Lumen," and filed on May 17, 2011.

* cited by examiner

ANNULOPLASTY RING WITH ANCHORS FIXED BY CURING POLYMER

CROSS-REFERENCE TO RELATED APPLICATIONS

This Application claims priority to U.S. Application No. 61/487,083, filed May 17, 2011, the entire contents of which are hereby incorporated by reference.

STATEMENT REGARDING FEDERALLY SPONSORED RESEARCH

Not Applicable

BACKGROUND OF THE INVENTION

This invention relates to an annuloplasty ring for repairing heart valves, and more particularly mitral valves.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

In an effort to stem the risk of heart valve disease, various medical procedures have been developed to repair or replace poorly functioning or stenosed heart valves. In particular, annuloplasty procedures have been used to repair heart valves by way of open heart surgery or, on a more limited basis, by way of less invasive techniques.

Mitral regurgitation is a particular type of heart valve disease wherein the mitral valve fails to sufficiently close, and blood is allowed to backflow across the valve. Consequently, many mitral annuloplasty procedures are designed to make the mitral annulus smaller, particularly in the septal—lateral dimension, allowing the mitral valve leaflets to coapt more effectively and preventing mitral regurgitation.

In some instances, repair of the mitral valve involves placing an annuloplasty ring on the mitral valve. Certain procedures involve suture-based cinching to reshape the mitral valve. In addition, some percutaneous annuloplasty procedures involve placing a rigid structure in the coronary sinus, which is near but not exactly at, the actual location of the mitral annulus. Such procedures can be cumbersome and may not be particularly effective or safe in all patients due to the anatomy of the coronary sinus, the mitral annulus, and the nearby circumflex coronary artery. In particular, coronary sinus devices may not be as effective as surgically placed devices, and crossing of the coronary sinus over the circumflex artery can cause dangerous compression of the artery by an annular cinching device placed in the coronary sinus.

Heretofore, reliable anchoring of an annuloplasty ring at a desirable location has been difficult using percutaneous and less invasive techniques. In addition, some prior attempts have utilized rather stiff structures in order to obtain the required shape and support for the valve. Consequently, there is a need for an annuloplasty procedure and device that overcomes the problems associated with prior approaches and devices.

SUMMARY OF THE INVENTION

In some embodiments, as discussed in more detail below, an annuloplasty device and method are provided for repairing a leaky heart valve, and in particular, a regurgitant mitral valve. In some embodiments, the annuloplasty device comprises an annuloplasty ring having a ring shell and a plurality of anchoring fasteners. The anchoring fasteners are deployed to attach to adjacent heart tissue.

The ring shell has a fill tube connected thereto. The ring shell is injected with a hardening polymer via the fill tube. The hardening polymer cures and maintains the ring shell in a desired shape to repair the leaky heart valve.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION

While this invention may be embodied in many different forms, there are described herein specific embodiments. This description is an exemplification of the principles of the invention and is not intended to limit it to the particular embodiments illustrated.

For the purposes of this disclosure, like reference numerals in the figures shall refer to like features unless otherwise indicated.

Figure 1:
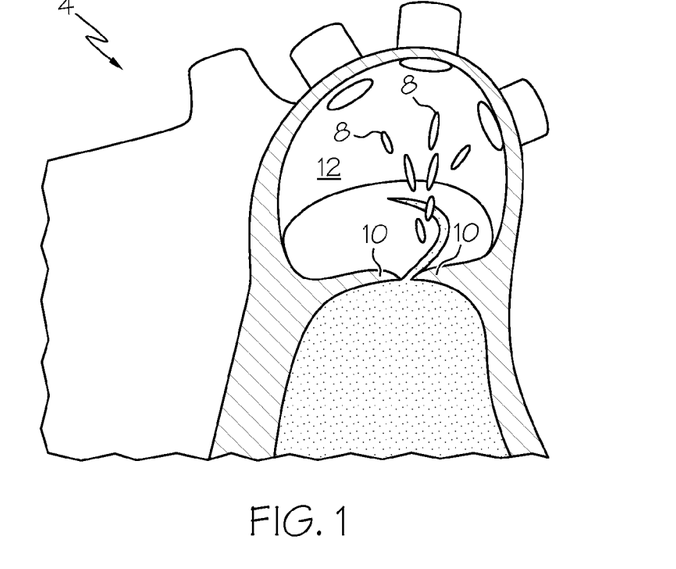
FIG. 1 is a partial cut-away view of a leaky heart valve.

Shown in FIG. 1 is a depiction of a regurgitant valve, more particularly a regurgitant mitral valve. As can be seen, blood 8 is backflowing past the regurgitant mitral valve 10 and back into the left atrium 12 of the heart 4.

Figure 2:
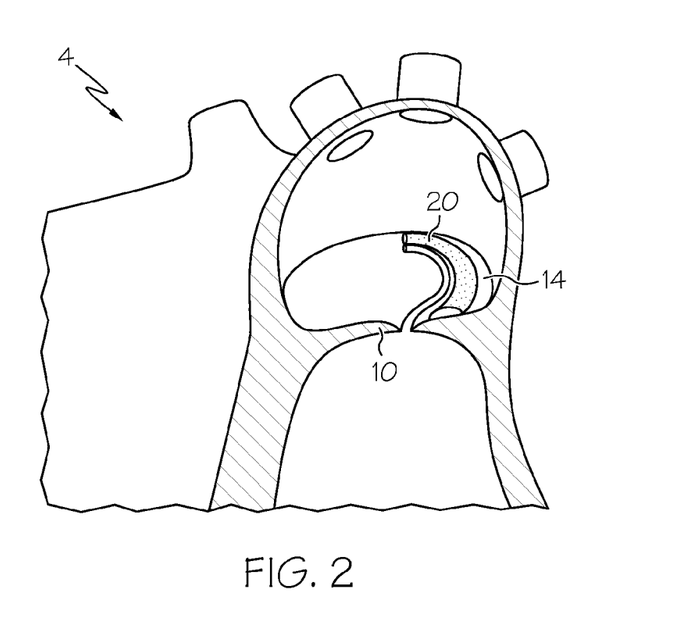
FIG. 2 is a partial cut-away view of a leaky heart valve with an annuloplasty ring attached adjacent to the valve.

In order to repair the regurgitant mitral valve 10 shown in FIG. 1, in some embodiments, an annuloplasty ring 20 (FIG. 2) is secured to a portion of the heart 4 at or near the mitral valve 10. As shown in FIG. 2, the annuloplasty ring 20 is placed on the atrial side of the mitral valve 10, for example, on the mitral annulus 14.

Figure 3:
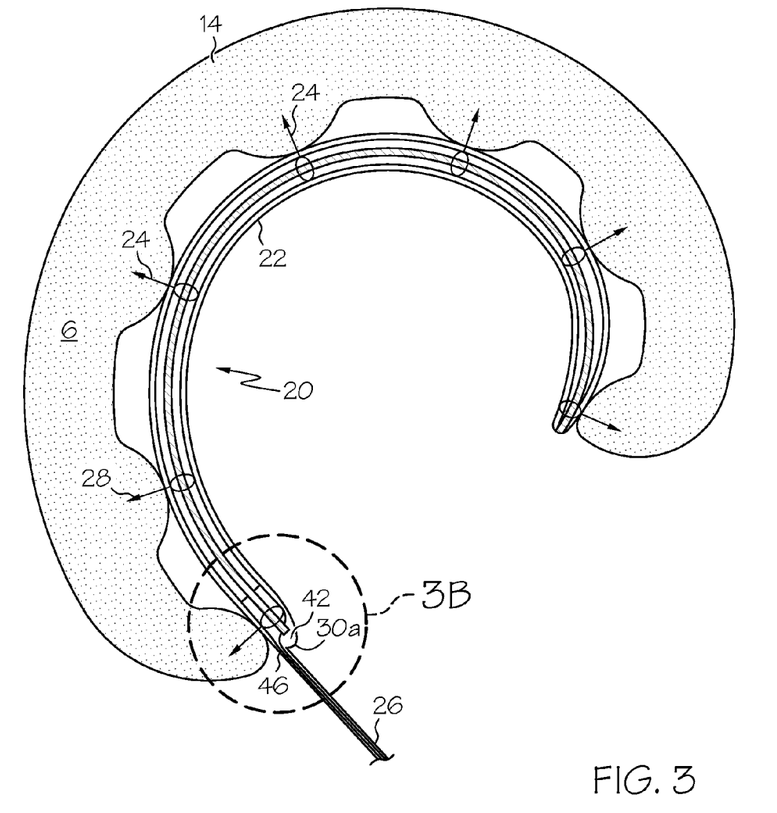
FIG. 3 is a top view of the mitral annulus having an annuloplasty ring attached thereto.

Turning to FIG. 3, a top view of the mitral annulus 14 is shown having an embodiment of the annuloplasty ring 20 of FIG. 2 attached thereto. As shown in FIG. 3, the annuloplasty ring 20 comprises a ring shell 22, a plurality of anchoring fasteners 24, and a fill tube 26.

In some embodiments, the ring shell 22 defines the outer wall of the annuloplasty ring 20. In some embodiments, the ring shell 22 comprises polyether block amide, or any other suitable material.

The anchoring fasteners 24 are configured to attach the annuloplasty ring 20 to the adjacent heart tissue 6. In some embodiments, for example as shown in FIG. 3, the anchoring fasteners 24 have a barb 28 or plurality of barbs. The barbs 28 prevent the anchoring fasteners 24 from pulling out of the heart tissue 6 upon deployment of the fasteners 24, thereby securing the annuloplasty ring 20 to the adjacent heart tissue 6. In some embodiments, the anchoring fasteners 24 extend through the material of the ring shell 22.

In some embodiments, the anchoring fasteners 24 are fastened to the outer surface of the ring shell 22. Moreover, in some embodiments, the anchoring fasteners 24 comprise a portion of the outer surface of the ring shell 22.

Figure 4:
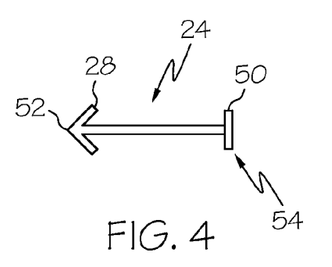
FIGS. 4 and 4A show an embodiment of an anchoring fastener.
Figure 4A:
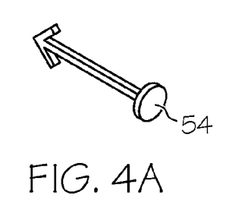
Figure 5:
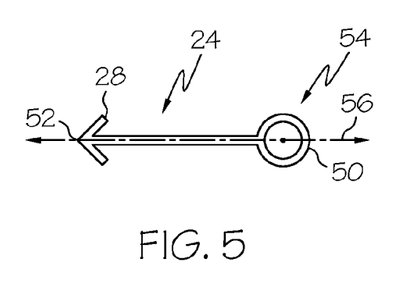
FIGS. 5 and 5A show an embodiment of an anchoring fastener.
Figure 5A:
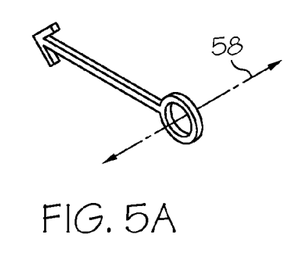

Turning to FIG. 4, in some embodiments, the anchoring fasteners 24 comprise a first end 50 and a second end 52. The second end 52 comprises a plurality of barbs 28 and the first end 50 comprises a base member 54. In some embodiments, the base member 54 comprises a circular cross section, for example as shown in FIG. 4A, with a disc or wafer-like shape. The base member 54 can also have any suitable shape, for example, rectangular, ovoid, or elliptical. In addition, in some embodiments, the base member 54 has an annular shape, for example as shown FIGS. 5 and 5A. The annularly shaped base member 54 can be oriented as shown in FIGS. 5 and 5A, such that the longitudinal axis 56 of the anchoring fastener 24 is perpendicular to the axis 58 of the annularly shaped base member 54, or can be oriented such that the longitudinal axis 56 of the anchoring fastener 24 is parallel or skewed relative to the axis 58 of the annularly shaped base member 54.

Figure 6:
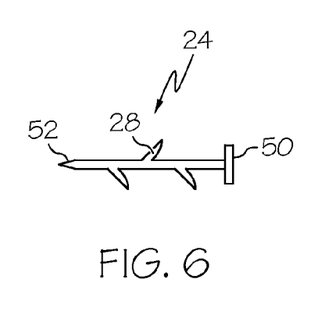
FIG. 6 shows an embodiment of an anchoring fastener.

In some embodiments, for example as shown in FIGS. 4 and 4A, the barbs 28 are positioned at the second end 52 of the anchoring fastener 24. In some embodiments, however, and as shown in FIG. 6, the barbs 28 are disposed along the length of the anchoring fastener 24, between the first and second ends, 50, 52.

Figure 3A:
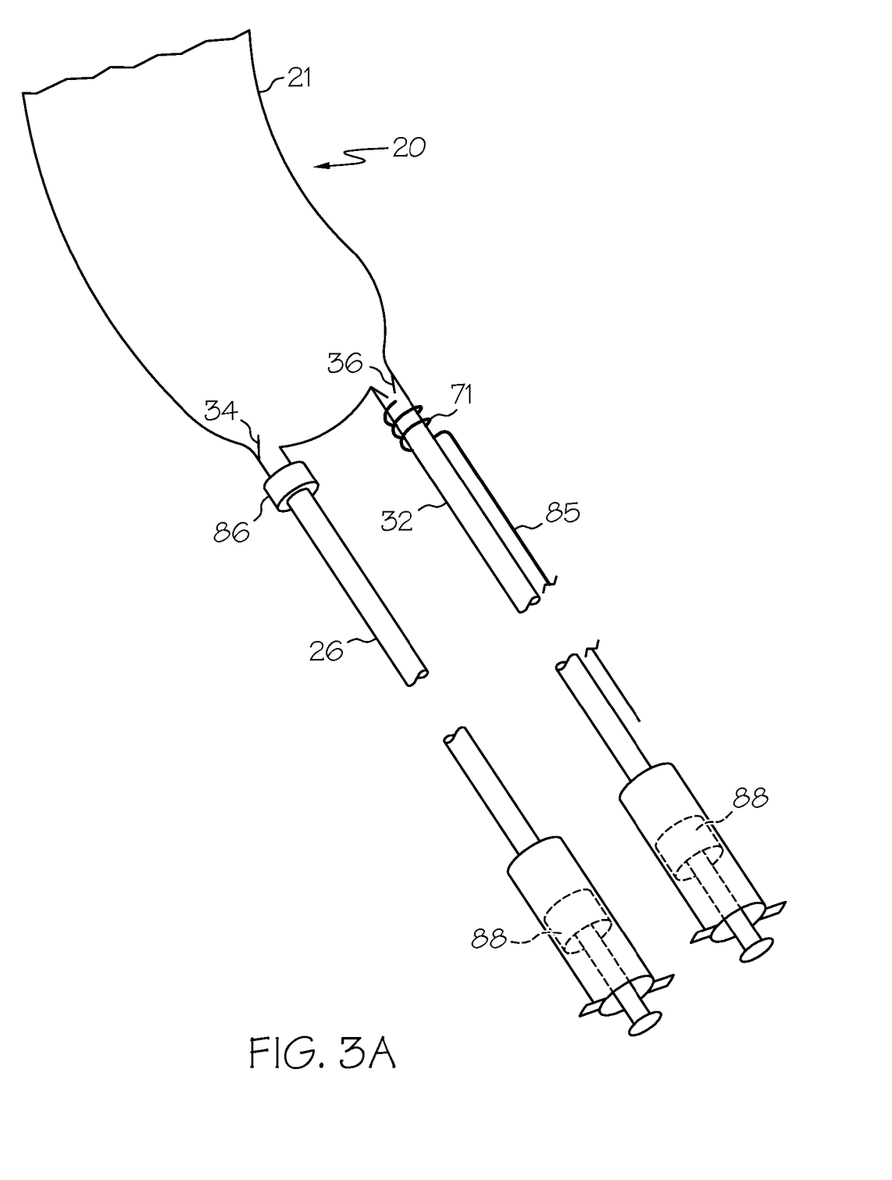
FIG. 3A shows a detailed view of an embodiment of the annuloplasty ring.
Figure 3B:
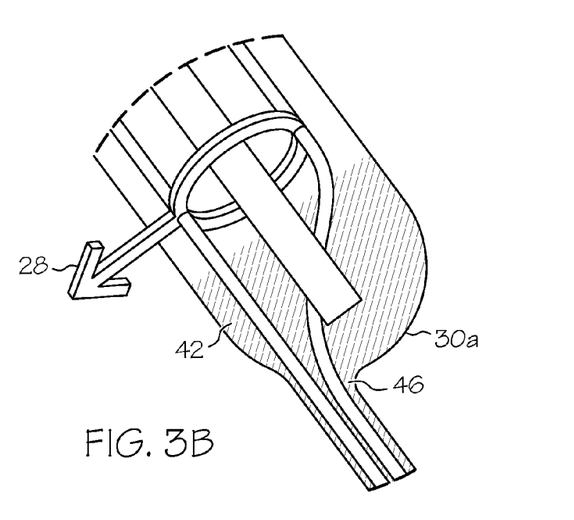
FIG. 3B shows a detailed view of a portion of the annuloplasty ring shown in FIG. 3.

Returning to FIG. 3 and the fill tube 26, in some embodiments the fill tube 26 is connected to an end 30a of the ring shell 22. In some embodiments, the fill tube 26 is connected to the ring shell 22 at an injection port 46. The fill tube 26 is used to inject a hardening polymer 42 into the ring shell 22 (FIG. 3B). The fill tube 26 can also be used to inject a contrast agent 44 (FIG. 7A) into the ring shell 22. In some embodiments, the contrast agent 44 is injected prior to the hardening polymer 42, and in some embodiments, along with the hardening polymer 42. In some embodiments, the contrast agent 44 comprises barium sulfate, iodine compounds, metallic particles, gas bubbles, carbon dioxide, saline, and any other suitable substance to improve the visibility of the ring shell 22.

Leakage of the contrast agent 44 or hardening polymer 42 into the patient's bloodstream is undesirable. Consequently, in some embodiments, the ring shell 22 comprises an elastomeric material which seals around the anchoring fasteners 24 upon their deployment. Then, as the hardening polymer 42 is injected into the ring shell 22, leakage of the hardening polymer out of the ring shell is minimized or altogether prevented.

Figure 7:
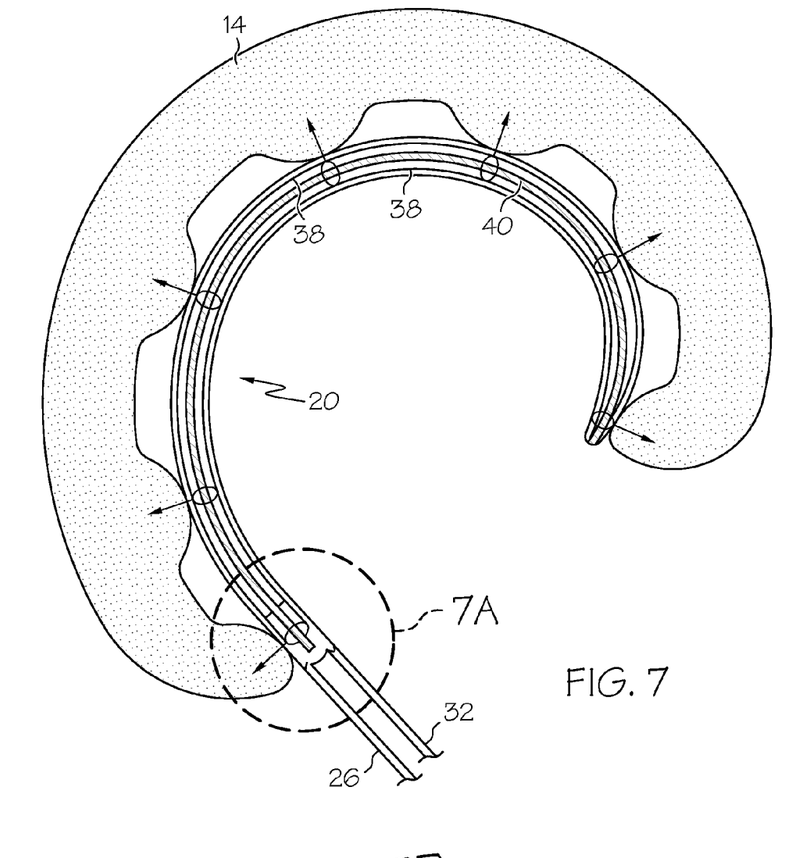
FIG. 7 is a top view of the mitral annulus having the annuloplasty ring of FIG. 3A attached thereto.
Figure 7A:
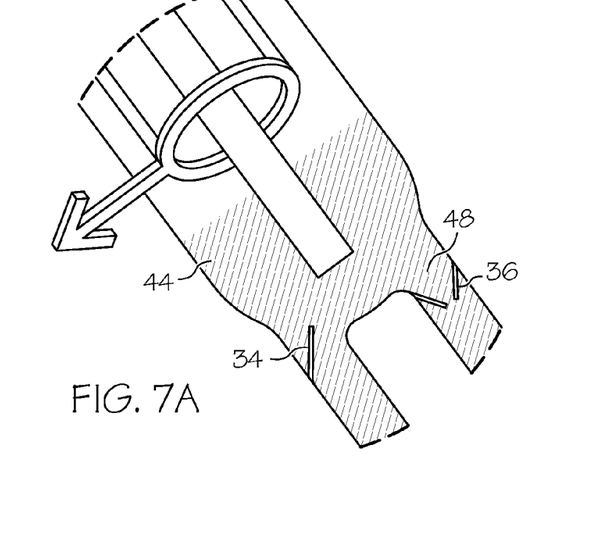
FIG. 7A shows a detailed view of a portion of the annuloplasty ring of FIG. 7

In addition to the foregoing, in some embodiments, for example as shown in FIG. 7, the annuloplasty ring 20 comprises a drain tube 32. In some embodiments, the contrast agent 44 can be extracted via the drain tube 32. In some embodiments, the drain tube 32 is connected to the ring shell 22 at drain port 48.

Moreover, in some embodiments, the fill tube 26 and drain tube 32 have valves 34, 36 disposed at the ends thereof. In some embodiments, the fill tube valve 34 comprises a check valve, allowing for one-way flow of fluid (e.g., hardening polymer 42 or contrast agent 44). In some embodiments, for example as shown in FIG. 3A, the fill tube valve 34 comprises a flap of material having a normally closed configuration. The flap opens when pressure is applied on the upstream side of the valve 34 via fluid. In some embodiments, the fill tube valve 34 comprises a leaflet valve, duckbill valve, or any other suitable valve.

In some embodiments, the drain tube valve 36, as shown for example in FIG. 3A, comprises a duckbill valve having a normally closed configuration. When the pressure inside the annuloplasty ring 20 (or a balloon 60 within the annuloplasty ring, as discussed in greater detail below) becomes sufficiently high, the drain tube valve 36 opens, releasing fluid out of the annuloplasty ring 20 and into the drain tube 32. In some embodiments, the drain tube valve 36 comprises a leaflet valve, flap valve (e.g., as described above with respect to the fill tube valve 34), or any other suitably configured valve.

As further depicted in FIG. 3A, in some embodiments, the fill tube 26 and drain tube 32 have a disconnect coupler 86 at their distal end. Although only fill tube 26 is depicted with the disconnect coupler, it will be appreciated that both of the fill tube 26 and drain tube 32 disclosed herein can incorporate the disconnect coupler 86. The disconnect coupler 86 permits the fill tube 26 to be disconnected from the annuloplasty ring 20, for example after the annuloplasty ring 20 has been placed and secured to the adjacent heart tissue. In some embodiments, the fill tube 26 is removed from the annuloplasty ring 20 by rotating or twisting the tube 26 to decouple it and remove it from the patient.

In some embodiments, the valves 34, 36 are closed prior to the tubes 26, 32 being decoupled from the annuloplasty ring 20. In this way, the hardening polymer 42 that has been inserted into the annuloplasty ring 20 will not spill out into the patient's blood. In addition, prior to decoupling the tubes 26, 32, a negative pressure can be drawn on the upstream side of the disconnect coupler 86, thereby withdrawing any residual fluid at or near the disconnect coupler 86. In some embodiments, the plungers 88 at the proximal end of the catheter can be pulled out to create the negative pressure in tubes 26, 32. This procedure will further prevent fluid from entering the patient's blood stream.

In some embodiments, the drain tube 32 is disconnected from the ring shell 22 fusible closure 71. In addition, although only the drain tube 32 is shown with the fusible closure 71, the fill tube 26 can also incorporate a fusible closure 71. In addition to the fusible closure 71, the annuloplasty ring 20 has an electrical wire 85 running along the drain tube 32. A portion of the electrical wire 85 is wound around the drain tube 32 at the fusible closure 71. To release the drain tube 32 from the body portion 21 of the annuloplasty ring 20, the electrical wire is pulled taught, thereby cinching the drain tube 32 closed. Subsequently, current is directed through the electrical wire 85 which heats the drain tube 32 until it is severed from the body portion 21 of the annuloplasty ring 20.

In some embodiments, for example as shown in FIGS. 3 and 7, the annuloplasty ring 20 further comprises at least one control wire 38 disposed within the ring shell 22. In some embodiments, the annuloplasty ring 20 has a plurality of control wires 38, for example two control wires 38, as seen in FIGS. 3 and 7. In combination, the two control wires 38 of FIGS. 3 and 7 are used to extend the anchoring fasteners 24 into adjacent heart tissue 6.

Figure 8:
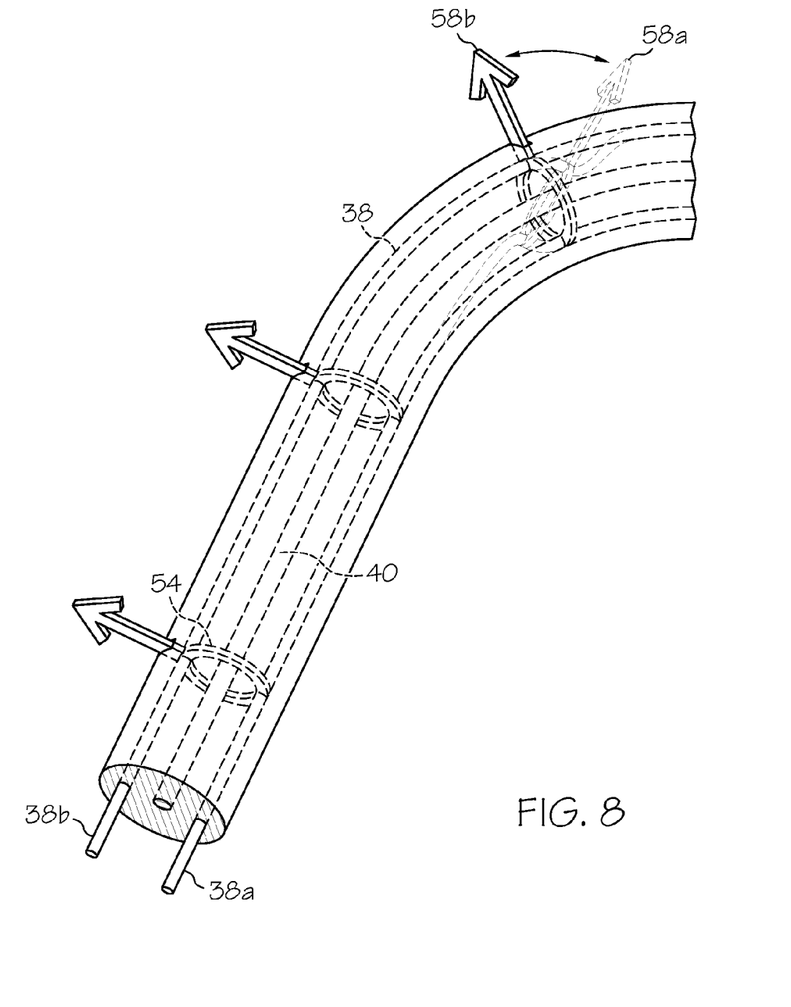
FIG. 8 is a partial cut-away view of the annuloplasty ring of FIG. 7.

Turning to FIG. 8, in some embodiments, the control wires 38 are connected to the base member 54 of the anchoring fasteners 24; for example, one of the control wires 38*a* is connected to the base member 54 nearer (or at) the first end 50 of the anchoring fastener 24, while the other control wire 38*b* is connected to the base member 54 nearer the second end of the anchoring fastener 24. In this way, one of the control wires, 38*a* can be pulled while the other control wire 38*b* is pushed, thereby moving the anchoring fasteners 24 from a retracted configuration 58*a* to an extended configuration 58*b*. The anchoring fasteners 24 remain in the retracted configuration 58*a*, for example, during insertion of the annuloplasty ring through the patient's vasculature and heart cavities.

In addition, in some embodiments, the control wires 38 are manipulated to aid in forming the desired shape of the annuloplasty ring 20, similar to steering a catheter. In some embodiments, the control wires comprise stainless steel, titanium, MP35N, or NiTi. Other suitable materials are also acceptable.

In some embodiments, the annuloplasty ring 20 further comprises a stiffening member 40. In some embodiments, the stiffening member 40 provides the annuloplasty ring 20 with a predetermined shape. In some embodiments, the stiffening member 40 comprises a resilient material which "springs" into its predetermined shape, upon placement of the annuloplasty ring 20 in the desired location of the patient's heart. In some embodiments, the stiffening member 40 comprises a shape memory material, for example, nitiniol; the stiffening member 40 can also comprise any other suitable material, for example, stainless steel, titanium, MP35N, and combinations thereof.

In some embodiments, the stiffening member 40 comprises a tension wire. In some embodiments, the tension wire is inserted into the annuloplasty ring 20 after placement of the annuloplasty ring 20 within the heart 4. Moreover, in some embodiments, the tension wire is inserted into the annuloplasty ring 20 after deployment of the anchoring fasteners 24.

Figure 9:
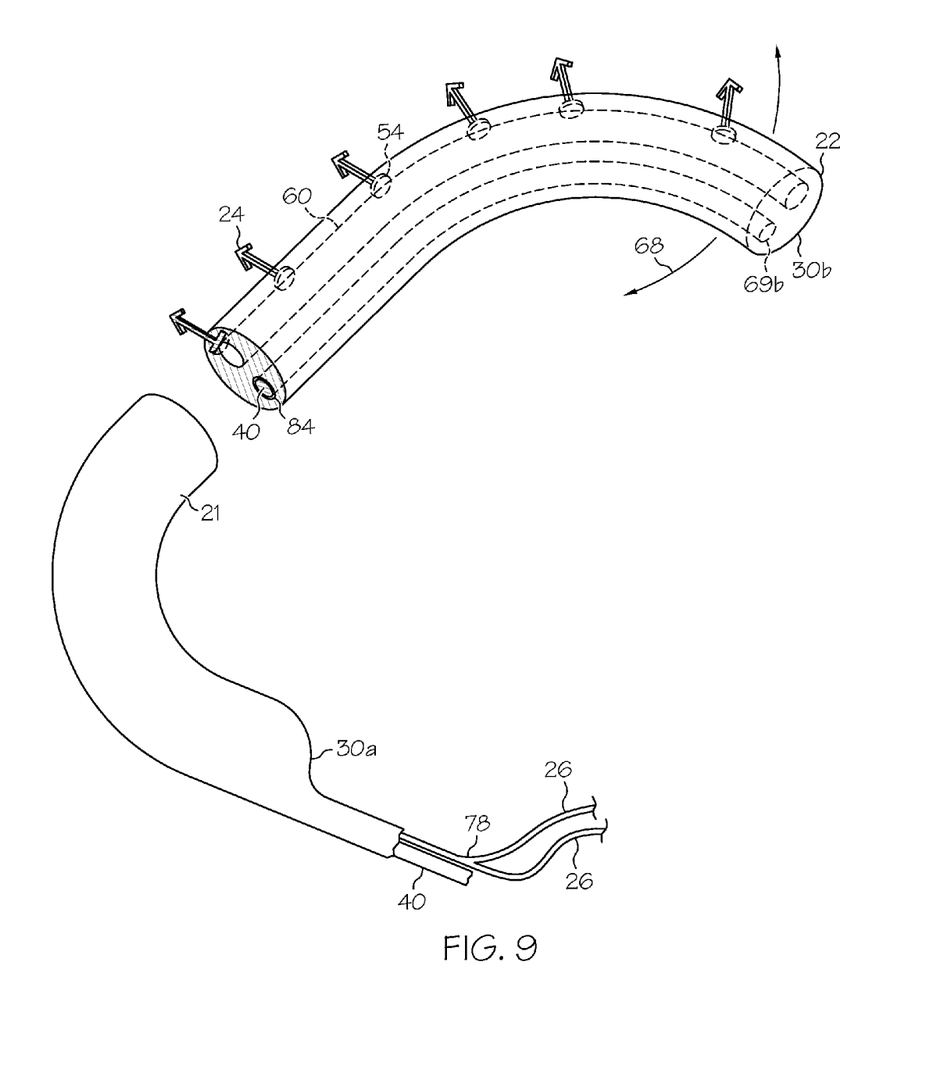
FIG. 9 is a partial cut-away view of an annuloplasty ring having an expandable balloon therein.

In some embodiments, for example as shown in FIG. 9, the stiffening member 40, in the form of a tension wire, extends along the length of the annuloplasty ring 20 and exits the end of the annuloplasty ring 20. In some embodiments, the stiffening member 40 extends outside the annuloplasty ring 20 and exits the patient's body. In this way, the stiffening member 40 is moveable or adjustable after the annuloplasty ring 20 has been placed within the heart 4, for example by manipulating the end of the stiffening member outside the patient's body, to rotate or otherwise adjust the positioning of the stiffening member 40. In some embodiments, the stiffening member 40 causes the annuloplasty ring 20 to take on the desired shape, for example by pulling the ends of the annuloplasty ring 20 towards one another, and, because the annuloplasty ring 20 is anchored to the surrounding heart tissue 6, alter the configuration of the adjacent mitral valve.

Furthermore, the stiffening member 40 comprises a distal end 69*b*. In some embodiments, the distal end 69*b* is anchored to the ring shell 22, and, in some embodiments, the distal end 69*b* is anchored to the distal end 30*b* of the ring shell 22. In addition, in some embodiments, the proximal end 30*a* of the ring shell 22 is moveable with respect to the stiffening member 40. The shape of the annuloplasty ring 20 can thereby be altered by pushing or pulling on the stiffening member 40 relative to the ring shell 22. In this regard, and in some embodiments, the when the stiffening member 40 is pulled relative to the ring shell 22, the ends 30*a* and 30*b* of the ring shell 22 move towards one another as shown with directional arrows 68. Moreover, when the stiffening member 40 is pushed relative to the ring shell 22, the ends 30*a* and 30*b* tend to move away from each other and the annuloplasty ring 20 assumes a straighter configuration. In this way the shape of the annuloplasty ring 20 is adjusted in accordance with the desired shape of the adjacent heart tissue, which is correspondingly adjusted as the stiffening member 40 is oriented within the ring shell 22.

Figure 9A:
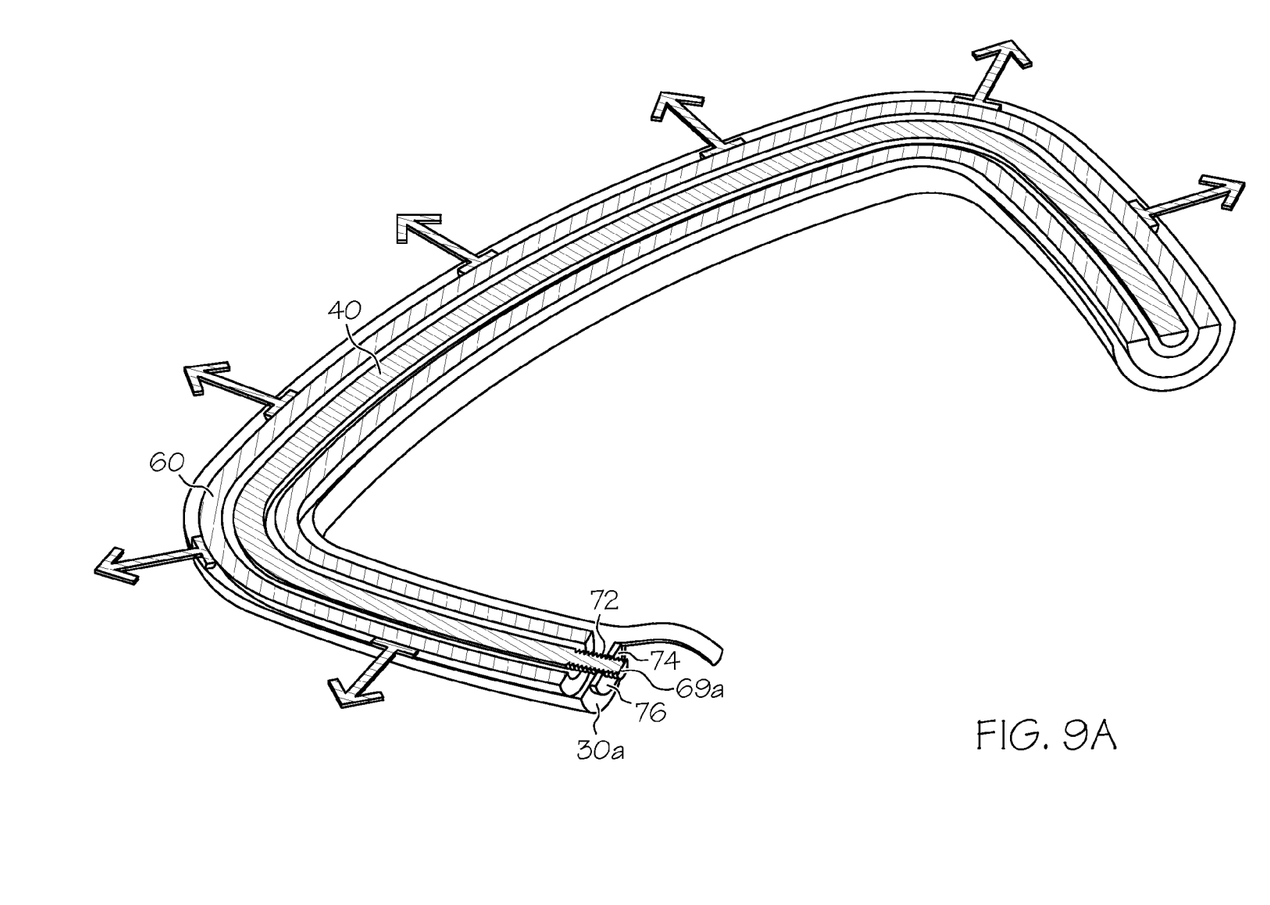
FIG. 9A is a partial cut-away view of an annuloplasty ring.

In some embodiments, for example as shown in FIG. 9A, the proximal end 69*a* of the stiffening member 40 has threads 72. The annuloplasty ring 20 has a threaded fastener 74 disposed at the proximal end 30*a* of the ring shell 22. In some embodiments, the threaded fastener 74 comprises a nut 76 having threads that are engaged to the threads 72 of the stiffening member 40. In this way, the stiffening member 40 is adjusted by rotating the threaded fastener 74. Rotating the threaded fastener 74 in one direction extends the stiffening member 40 out of the ring shell 22, while rotating the threaded fastener 74 in the opposite direction pushes more of the stiffening member 40 into the ring shell. The threaded fastener 74 is stationed at the proximal end 30*a* of the ring shell 22.

In some embodiments, the stiffening member 40 comprises a non-magnetic material, for example, to be MRI (Magnetic Resonance Imaging) compatible. The stiffening member 40 can comprise any desirable cross-section, for example, circular, ovoid, rectangular, I-beam, or it can have a non-uniform cross-section; for example, it can be wider nearer the proximal end that the distal end, or it can be wider nearer the middle and narrower at the proximal and distal ends.

In some embodiments, the stiffening member 40 is contained within a sleeve 84, for example as shown in FIG. 9. As such, the sleeve 84 acts as a barrier between the stiffening member 40 and the balloon 60, in the embodiment shown in FIG. 9.

Moreover, in some embodiments, the ring shell 22 has a preset shape which is counteracted by the stiffening member 40 during insertion of the annuloplasty ring 20. In this way, during insertion of the annuloplasty ring 20, the device has a predetermined straight or linear configuration, but is flexible in order to navigate the patient's vasculature. Then, upon removal of the stiffening member 40 from the annuloplasty ring 20, the annuloplasty ring 20 relaxes into its preset shape, for example a "D" shape, to be attached to the mitral annulus 14. Moreover, in some embodiments, for example where the ring shell 22 has a stiffening member 40 therein, the anchoring fasteners 24 have an annular base member, for example as shown in FIGS. 5 and 5A. In some embodiments, for example as shown in FIG. 8, the stiffening member 40 is disposed through the annularly shaped base member 54.

In some embodiments, for example as shown in FIG. 9, the anchoring fasteners 24 can be extended by way of a balloon 60. The balloon 60 is inflated, pushing outwardly on the base members 54 of the anchoring fasteners 24, thereby extending the anchoring fasteners 24 into the adjacent heart tissue.

Figure 10:
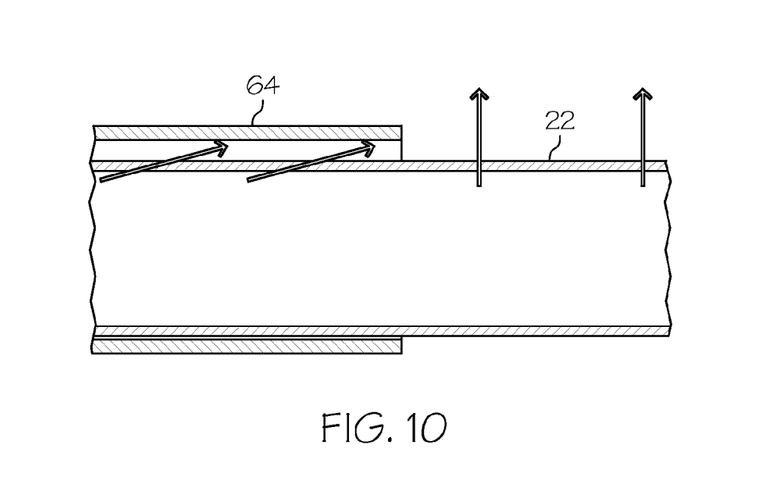
FIG. 10 is a side view of an annuloplasty ring having an expandable sheath.

In some embodiments, for example as shown in FIG. 10, the annuloplasty ring comprises a sheath 64. The sheath 64 is placed exteriorly to the ring shell 22 during insertion of the annuloplasty ring 22. As shown in FIG. 10, the sheath 64 is in a partially removed configuration. As the sheath 64 is removed, the anchoring fasteners 24 are permitted to extend outwardly into adjacent heart tissue. Prior to extension of the anchoring fasteners 24, however, the anchoring fasteners 24 are restrained by the sheath 64.

Figure 9B:
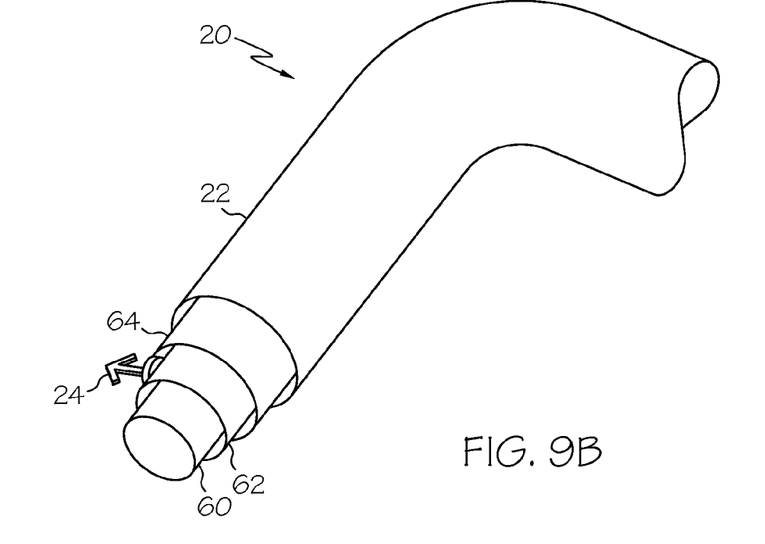
FIG. 9B is a partial view of an annuloplasty ring having an inner balloon.

Turning now to FIG. 9B, in some embodiments, the annuloplasty ring 20 comprises an outer ring shell 22, a sheath 64, a mesh expander 62, and a balloon 60. As shown in FIG. 9B, the ring shell 22 comprises the outer most layer of the annuloplasty ring 20. Prior to deployment of the anchoring fasteners 24, a sheath 64 prevents the anchoring fasteners 24 from protruding outwardly through the ring shell 22. As the sheath 64 is removed, for example as discussed above with respect to FIG. 10, the mesh expander 62 pushes the anchoring fasteners 24 outwardly through the ring shell 22.

In some embodiments, the mesh expander 62 is self-expanding. In some embodiments, the mesh expander 62 comprises a braided or woven mesh, for example, of NiTi wires. In some embodiments, the mesh expander 62 and the anchoring fasteners 24 comprise a unitary structure, wherein some of the wires of the mesh expander 62 protrude outwardly from the body of the mesh expander 62.

In addition, in some embodiments, the balloon 60 is disposed within the mesh expander 62. In some embodiments, the balloon 60 is filled with the hardening polymer 42. In some embodiments, for example where the balloon 60 is filled with the hardening polymer 42, the hardening polymer 42 is sealed off from the remainder of the annuloplasty ring 20. Isolating the hardening polymer 42 to balloon 60 minimizes the risk of hardening polymer 42 from seeping into the adjacent components of the annuloplasty ring 20 or into the patient's blood.

Further, in some embodiments, the balloon 60 is expanded to facilitate expansion, or further expansion, of the mesh expander 62.

In some embodiments, the balloon 60 and the ring shell 22 comprise the same material. Alternatively, the balloon 60 and the ring shell 22 ca comprise different materials.

In some embodiments, the ring shell 22 can be folded over itself along its length with the anchoring fasteners 24 being disposed inside the folds of the ring shell during insertion of the annuloplasty ring 20.

Figure 11:
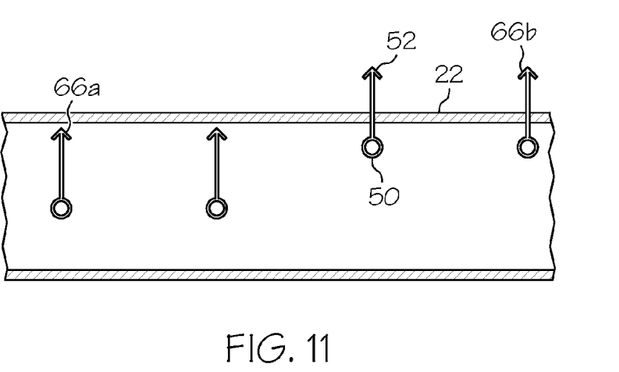
FIG. 11 is a side view of an embodiment of an annuloplasty ring.

Turning now to FIG. 11, in some embodiments, the anchoring fasteners 24 are extended from a first configuration 66a, for example during insertion of the annuloplasty ring 20 through the patient's vasculature, to a second configuration 66b, for example to affix the annuloplasty ring 20 to the heart tissue. As shown in FIG. 11, in the first configuration 66a, the anchoring fasteners 24, in their entirety, are contained within the ring shell 22. Upon extension of the anchoring fasteners 24, however, the second end 52 of the anchoring fasteners is extended outwardly through the ring shell 22.

Returning now to the hardening polymer 42, the hardening polymer 42 can be hardened by chemical reaction, for example by admixing two components within the ring shell 22 or just prior to injection of the hardening polymer 42 in the ring shell. In some embodiments, a catalyst is added to the hardening polymer 42 to facilitate hardening. Moreover, the hardening polymer 42 can be cured by way of heating, ultraviolet (UV) activation, or any other suitable method. After the hardening polymer 42 has hardened, it secures the annuloplasty ring 20 in the smaller, cinched or shrunk configuration.

In some embodiments, the hardening polymer 42 comprises a two-part biocompatible polymer. In some embodiments, the hardening polymer 42 comprises a foam and in some embodiments, the hardening polymer 42 has a matrix of reinforcing fibers added to it to form a composite material. In some embodiments, the reinforcing fibers are added to the polymer matrix to provide additional strength. In some embodiments, the reinforcing fibers are ultraviolet (UV) transmissive (e.g., quartz) to provide both increased strength and a path through which to cure UV-hardening polymers. In some embodiments, reinforcing fibers are deployed within the ring shell 22 or another lumen or balloon as a complete bundle, in several smaller bundles, or one at a time. Also, in some embodiments, the distal surface of UV transmissive fibers is textured, abraded, etched, or otherwise treated to enhance lateral dispersion of the UV light into the hardening polymer 42.

To facilitate mixing of the two-part hardening polymer, the annuloplasty ring 20 has two fill tubes 26 that are joined together at mixing joint 78. In some embodiments, each of the two fill tubes 26 is filled with one part of a two-part hardening polymer. For example, fill tube 26a is filled with the resin while fill tube 26b is filled with the hardener. In this way, the individual components of the two-part hardening polymer are independently routed through the patient's vasculature and mixed immediately prior to their introduction into the body portion 21 of the annuloplasty ring 20.

Figure 12:
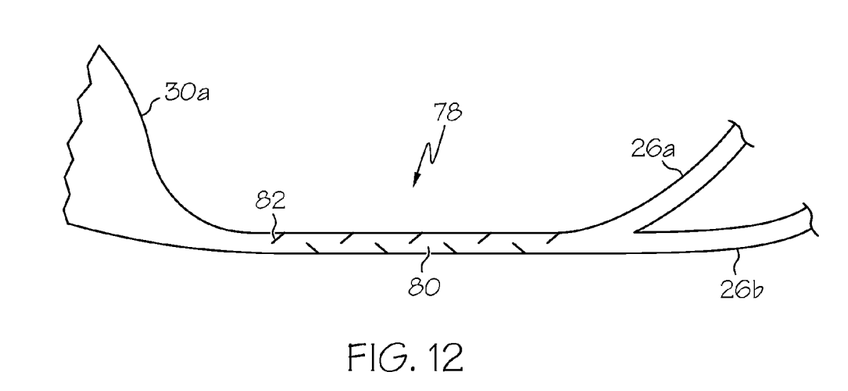
FIG. 12 is a detailed view of an embodiment of a mixing joint of the annuloplasty ring.

In some embodiments, for example as shown in FIG. 12, the mixing joint 78 comprises a mixing chamber 80. In some embodiments, the mixing chamber 80 comprises a plurality of vanes 82 that facilitate mixing of the individual components. In some embodiments, the mixing chamber is similar to a two-part epoxy mixing nozzle.

In some embodiments, the two-part hardening polymer 42 is mixed outside of the patient's body and is routed through the fill tube 26 in a pre-mixed state. In this instance, the hardening polymer 42 has a long enough cure time to permit adjustment of the shape of the annuloplasty ring 20 after the hardening polymer 42 has been injected into it and after the fill tubes 26 have been severed from the annuloplasty ring 20 and removed from the patient. Consequently, the hardening polymer 42 will not cure in the fill tubes 26 while the fill tubes are still disposed within the patient's vasculature. In some embodiments, the hardening polymer 42 has a cure time of between about 2 and 30 minutes. In some embodiments, the hardening polymer has a cure time of between about 4 and 10 minutes. Moreover, in some embodiments, for example, where the components of the hardening polymer 42 are mixed within the patient's vasculature, the hardening polymer 42 has a cure time of between about 2 and 5 minutes.

Figure 13:
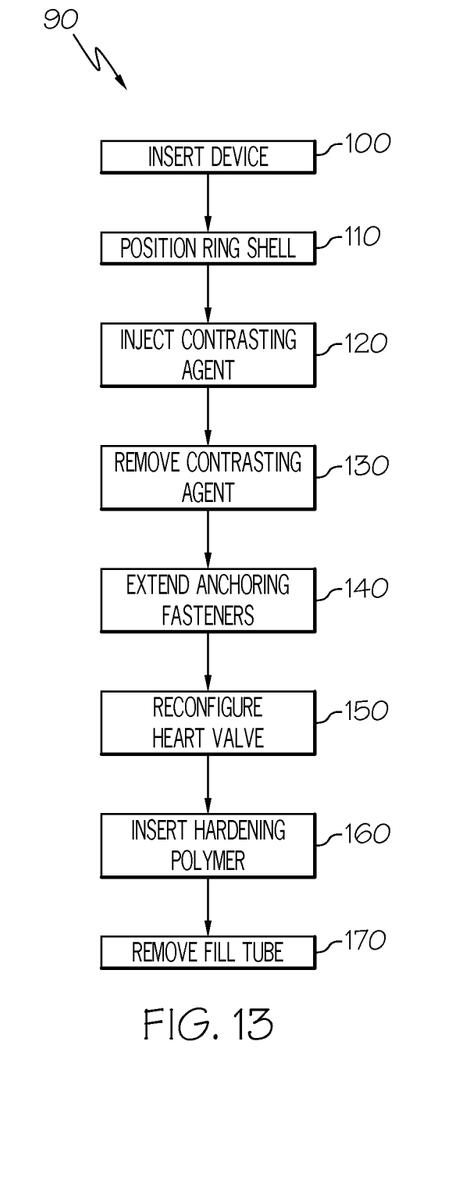
FIG. 13 is a flow chart depicting a method for inserting and deploying an annuloplasty ring.

Shown in FIG. 13 is a method 90 for inserting and deploying the annuloplasty ring 20. In step 100, the ring shell 22 is inserted into the patient's vasculature by way of a catheter. In some embodiments, the ring shell 22 is inserted across the atrial septum, through the foramen ovale, and into the left atrium, adjacent to the mitral annulus 14. In step 110, the ring shell 22 is then positioned at the desired location, for example, at or near the mitral annulus 14 in the patient's heart 4. In some embodiments, the distal end 30b of the ring shell 22 is anchored before the remainder of the ring shell 22. In this case, in some embodiments, the distal anchoring fastener 24 is not an integral part of the ring shell 22 and is deployed and anchored via a guidewire and/or guide catheter. Once the distal anchoring fastener 24 has been correctly placed, the ring shell 22 is deployed over the guidewire and/or guide catheter, which remains attached to the distal anchoring fastener 24. The ring shell 22 is advanced over the guidewire until it reaches the distal anchoring fastener 24. And, further advancement of the ring shell 22 will cause the ring shell 22 to begin bending along the margin between the mitral valve and the septal wall. Subsequently, at step 120, the contrast agent 44 is injected into the ring shell 22 via fill tube 26 and fill tube valve 34. Positioning of the ring shell 22 can then be adjusted and verified to follow the mitral valve annulus as the ring shell 22 is advanced into the left atrium. As the ring shell 22 is advanced, it may only be partially filled with contrast agent 44 to allow more flexibility of the annuloplasty ring 20, which, in some embodiments, is needed to achieve proper positioning. In some embodiments, steps 110 and 120 are carried out in reverse order or simultaneously. In some embodiments, for example where the ring shell 22 is already sufficiently radiopaque, the method 90 will be performed without step 120. Where the contrast agent 44 is injected in accordance with step 120, however, in some embodiments, the contrast agent 44 will subsequently be removed via drain tube 32 and drain tube valve 36 in accordance with step 130. Then, as shown in step 140, the anchoring fasteners 24 are extended into the adjacent heart tissue 6. The anchoring fasteners 24 are extended, for example (and as discussed above) by removal of the sheath 64, inflation of the balloon 60, inflation of a mesh expander, actuation of the control wires 38, or in any other suitable manner.

In the instance where the anchoring fasteners 24 are deployed by removal of a sheath 64, in some embodiments, the anchoring fasteners 24 are extended and anchored sequentially, starting at the distal end, as each anchoring fastener 24 is exposed. This allows the sheath 64 to be positioned and anchored on small segments of the mitral annulus, which, in some embodiments, simplifies the process.

After the anchoring fasteners 24 are extended, the annuloplasty ring 20 is shrunk or rearranged to reconfigure the mitral valve 10, thereby repairing the leaky mitral valve 10, as is shown at step 150. The anchoring fasteners 24 pull the heart tissue 6, to which they are anchored, along with the ring shell 22 as the annuloplasty ring is shrunk or rearranged. In some embodiments, the mitral annulus 14 is shortened in a septal-lateral dimension. In some embodiments, the ring shell 22 is shrunk by the actuation of cinch filaments, release of spring force, removal or addition of the stiffening member 40, or any other suitable method.

As shown in step 160, a hardening polymer 42 is inserted into the ring shell 22. In some embodiments, the hardening polymer 42 surrounds the first ends 50 of the anchoring fasteners 24, and the portions of the anchoring fasteners 24 that are within the ring shell 22. The hardening polymer 42 subsequently solidifies in the ring shell 22. Upon curing, the hardening polymer 42 provides the ring shell 22 with additional strength and support. Moreover, after the hardening polymer 42 has cured, it prevents the anchoring fasteners 24 from retracting back into the ring shell 22.

In some embodiments, addition of the hardening polymer 42 forces the contrast agent 44 out of the ring shell though drain tube 32. In addition, in some embodiments, the hardening polymer 42 is mixed with the contrast agent 44 to provide, for example, a radiopaque hardening polymer. In this case, the contrast agent 44 is not drained or forced out of the ring shell.

Next, in accordance with the method shown in FIG. 13, the fill tube 26, and, if present, drain tube 32 is disconnected from the ring shell 22 and removed at process step 170. In some embodiments, step 170 is performed prior to final curing of the hardening polymer 42. Alternatively, in some embodiments, the hardening polymer 42 is cured prior to the fill tube 26 and drain tube 32 being disconnected. In the event that the fill tube 26 and drain tube 32 are disconnected prior to curing of hardening polymer 42, in some embodiments, the hardening polymer is retained in the ring shell 22 via fill tube valve 34 and drain tube valve 36.

In addition to the foregoing, the annuloplasty ring 20 can be attached to the heart in any desirable location, for example above or below the mitral valve, directly to the mitral annulus, in the ventricle adjacent to the annulus, or outside of the heart with the anchoring fasteners directed towards the annulus.

Although particular features are shown or described with respect to particular embodiments disclosed herein, it will be appreciated that these features can be combined with the features or substituted for the features of other embodiments.

In addition, the Applications entitled "Percutaneous Mitral Annulus Mini-Plication," with Application No. 61/487,065; "Positioning Cage," with Application No. 61/487,053; "Corkscrew Annuloplasty Device," with Application No. 61/487,063; and "Annuloplasty Ring with Piercing Wire and Segmented Wire Lumen," with Application No. 61/487,072, all of which were filed on May 17, 2011, are hereby incorporated by reference.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:
1. An annuloplasty device comprising:
a deployed configuration and an undeployed configuration;
a ring shell, the ring shell defining an outer surface of the device in the deployed configuration;
a plurality of anchoring fasteners each having a first end and a second end, the first end disposed within the ring shell; the second end extending exteriorly to the ring shell when the device is in the deployed configuration; and an expandable balloon disposed within the ring shell, the expandable balloon contacting the plurality of anchoring fasteners upon expansion of the expandable balloon;

wherein the annuloplasty device is configured to receive a hardening polymer within the ring shell.

2. The annuloplasty device of claim 1 further comprising a stiffening wire disposed within the ring shell.

3. The annuloplasty device of claim 1 further comprising a stiffening member disposed within the ring shell.

4. The annuloplasty device of claim 1 further comprising an injection port located on the ring shell.

5. The annuloplasty device of claim 4 further comprising at least one fill tube, the at least one fill tube connected to the injection port.

* * * * *